United States Patent [19]

Fahmy

[11] Patent Number: 4,496,552
[45] Date of Patent: Jan. 29, 1985

[54] O-HALOPHENYL O-ALKYL S-TERT-BUTYL PHOSPHOROTHIOATES AS PESTICIDES

[75] Inventor: Mohamed A. H. Fahmy, Princeton, N.J.

[73] Assignee: FMC Corporation, Philadelphia, Pa.

[21] Appl. No.: 487,773

[22] Filed: Apr. 22, 1983

[51] Int. Cl.³ ............... A01N 57/14; C07F 9/165
[52] U.S. Cl. ............................ 514/147; 260/964
[58] Field of Search .................... 260/964; 424/224

[56] References Cited

U.S. PATENT DOCUMENTS 3,784,654  1/1974  Kume et al. ................ 260/964
3,839,511 10/1974  Kishino et al. ............. 260/941

OTHER PUBLICATIONS

Aldrich Catalog Handbook of Fine Chemicals, 1981–1982, p. 868.
Drabek et al., "Syn. & Properties of O-Aryl-O-Alkyl-S-Alkyl Phosphorothioates", IUPAC, Int'l. Cong. Pest. Chem., 1979, part 2, pp. 130–134.

Primary Examiner—Anton H. Sutto
Attorney, Agent, or Firm—Robert L. Andersen; H. Robinson Ertelt

[57] ABSTRACT

Compounds of the formula

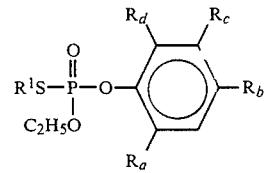

in which $R^1$ is tertiary butyl, $R_a$ and $R_b$ are each bromine or chlorine, and $R_c$ and $R_d$ are each hydrogen, bromine or chlorine, having superior residual activity against foliar feeding insects and acarids are disclosed and exemplified.

7 Claims, No Drawings

O-HALOPHENYL O-ALKYL S-TERT-BUTYL PHOSPHOROTHIOATES AS PESTICIDES

The present invention relates to novel compounds useful as insecticides, ovicides, acaricides and nematicides, to pesticidal compositions thereof, and to a method for controlling insects, acarids, and nematodes therewith. More particularly, the invention relates to O-aryl S-tertiary-butyl phosphorothioates in which the aryl group is halogen substituted.

Numerous O-aryl O-alkyl S-lower alkyl phosphorothioates have heretofore been reported to have insecticidal and nematicidal activity. The compounds described in the literature vary widely with respect to the substitution patterns on the O-aryl group, but are limited with respect to the S-lower alkyl group to primary and secondary alkyl groups. The compounds of the prior art are known to have high initial insecticidal activity but have very poor residual activity due to rapid degradation on exposure to air, light and other environmental factors present at the locus of application. This seriously limits the utility of the prior art compounds as foliar insecticides.

In order for a foliar insecticide to be most effective in controlling foliar feeding insects, it must have sufficient residual activity to enable it to be applied at economical use rates just prior to larval hatch and to remain effective through the normal hatching period, generally about 3 to 5 days. Alternatively and/or in addition, it would be desirable that the compound have ovicidal activity which would substantially reduce the larval hatch when applied at economical use rates.

The compounds previously described in the literature do not have such ovicidal activity or the required residual activity. To overcome these deficiencies it would be necessary to apply those compounds at high application rates to extend their residual activity or to apply multiple applications at closely spaced intervals. Both of these solutions are unsatisfactory and uneconomical.

It has now been found in compounds of the formula

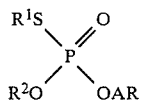

($R^1$ and $R^2$ are alkyl groups and AR is an optionally substituted phenyl group), improved residual activity may be obtained, in many instances together with ovicidal activity, by replacing the S-alkyl group ($R^1$) with a tertiary butyl group. This finding is particularly surprising in view of a recent publication concluding that activity is improved when the S-alkyl group is increased from ethyl to propyl, but declines as it is further increased to 4 or more carbon atoms, i.e. i-butyl, n-butyl, s-butyl, n-pentyl or n-decyl. See Drabek, J. and Fluck, V., SYNTHESIS AND PROPERTIES OF O-ARYL O-ALKYL S-ALKYL PHOSPHOROTHIOATES, IUPAC, International Congress of Pesticide Chemistry, 4th, Zurich, Switzerland, presented July 24-28, 1978, published 1979, part 2, pp 130-134 at 131.

In accordance with the foregoing, the present invention provides O-halophenyl S-tert-butyl phosphorothioates having the formula

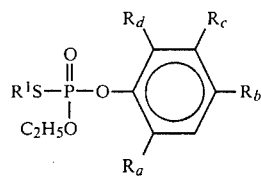

in which $R^1$ is a tertiary butyl group, $R_a$ and $R_b$ are each halogen, the same or different, $R_c$ is hydrogen or halogen, and $R_d$ is hydrogen or halogen. As used in the present application the terms halo or halogen mean halogen atoms selected from the group consisting of bromine or chlorine.

The preferred compounds are thus those in which O-halophenyl group is 2,4-dichlorophenyl, 2,4,5-trichlorophenyl, 2,4,6-trichlorophenyl, or 4-bromo-2-chlorophenyl.

These compounds may be prepared by reacting an O-aryl phosphoric chloride with tertiary butyl thiol as illustrated in the examples which follow. In these examples the assigned compound numbers are those subsequently used in reporting biological data.

EXAMPLE 1

Synthesis of O-ethyl O-2,4-dichlorophenyl S-tert-butyl phosphorothioate (Compound 1)

Step A: Synthesis of O-ethyl O-2,4-dichlorophenyl phosphoric chloride as an intermediate To a solution of 6.5 g (0.04 mole) of ethyl phosphoric dichloride and 5.5 g (0.034 mole) of 2,4-dichlorophenol in 75 ml of toluene cooled to 0° C. by an ice bath was added dropwise 3.4 g (0.034 mole) of triethylamine. After addition was completed the temperature was allowed to rise to ambient conditions and stirring was continued for 16 hours. The mixture was filtered. The filtrate was evaporated under reduced pressure, leaving a yellow oil as a residue. Hexane was added to the oil and this solution was filtered. After evaporating the hexane, O-ethyl O-2,4-dichlorophenyl phosphoric chloride was recovered as a yellow oil.

Step B: Synthesis of O-ethyl O-2,4-dichlorophenyl S-tert-butyl phosphorothioate To a suspension of 0.8 g (0.034 mole) of sodium hydride in 75 ml of tetrahydrofuran under nitrogen was added dropwise 3.1 g (0.034 mole) of 2-methyl-2-propanethiol. The mixture was warmed at 50° C. until hydrogen evolution ceased. After the mixture had cooled to ambient temperature, the O-ethyl O-2,4-dichlorophenyl phosphoric chloride from Step A was added. The mixture was stirred for approximately 16 hours. The tetrahydrofuran was evaporated under reduced pressure, and 75 ml of toluene was added to the residue. This solution was washed twice with 25 ml of water, once with 25 ml of a 5% aqueous sodium hydroxide solution, and once with 25 ml of water. The solution was dried over anhydrous sodium sulfate and filtered. The solvent was evaporated under high vacuum at 60° C. for two hours. Yield 7.4 g as an orange oil.
NMR (CDCl$_3$, ppm): 1.25–1.65(m,12H), 4.05–4.60(m,2H), 7.10–7.70(m,3H).

EXAMPLE 2

O-Ethyl O-4-bromo-2-chlorophenyl S-tert-butyl phosphorothioate (Compound (2) was prepared in the manner of Example 1 from O-ethyl O-4-bromo-2-chlorophenyl phosphoric chloride and 2-methyl-2-propanethiol. Yield, 6.2 g as a yellow oil. The yellow oil was crystallized from hexane to yield white crystals, mp 48° to 53° C.

NMR (CDCl$_3$, ppm): 1.30–1.60(m,12H), 4.10–4.60(m,2H), 7.40–7.65(m,3H).

EXAMPLE 3

O-Ethyl O-2,4,5-trichlorophenyl S-tert-butyl phosphorothioate (Compound 3) was prepared in the manner of Example 1 from O-ethyl O-2,4,5-trichlorophenyl phosphoric chloride and 2-methyl-2-propanethiol. Yield, 6.67 g as an orange oil. NMR (CDCl$_3$, ppm): 1.35–1.70(m,12H), 4.10–4.65(m,2H), 7.55–7.85(m,2H).

EXAMPLE 4

O-Ethyl O-2,4,6-trichlorophenyl S-tert-butyl phosphorothioate (Compound 4) was prepared in the manner of Example 1 from O-ethyl O-2,4,6-trichlorophenyl phosphoric chloride and 2-methyl-2-propanethiol. Yield, 3.9 g as a brown oil. NMR (CDCl$_3$, ppm): 1.20–1.70(m,12H), 4.10–4.60(m,2H), 7.35(s,2H).

While the compounds of this invention control nematodes and soil borne insects such as corn rootworm, they are most preferably used for control of insects which feed on the above ground portions of the plant. For nematode and rootworm control the compound may be applied to or incorporated into the soil in which crops are planted or are to be planted, or to the plant's roots. For control of pests attacking the above ground portions of the plant the compound is most suitably applied to the leaves and stems of the plant, i.e. by foliar application.

The compounds are generally not applied full strength but are typically applied as formulations which may be applied as such or further diluted for application. Typical formulations include compositions of the active ingredient in combination with one or more agriculturally acceptable adjuvants, carriers or extenders, frequently with a surface active agent, and optionally with other active ingredients. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like.

A typical formulation may vary widely in concentration of active ingredient depending upon the particular agent used, the additives and carriers used, other active ingredients, and the desired mode of application.

With due consideration to these factors the active ingredient of a typical formulation may, for example, be suitably present at a concentration of about 0.01% up to about 95%, preferably 0.1% up to 90%, of the formulation, agriculturally acceptable carriers, diluents, adjuvants, and other suitable active ingredients comprising the balance of the formulation. Compatible surface active agents, if employed in a formulation, may be present at various concentrations, suitably in the range of 1 to 30% by weight of the formulation.

The formulation may be used as such or diluted to a desired use dilution with a diluent or carrier suitable for facilitating dispersion of the active ingredients. A suitable concentration of the active ingredient in the use dilution may be in the range of 0.0001% to 10%, more preferably 0.01% to about 10%, by weight.

Many variations of spraying, dusting, and controlled or slow release compositions of a type known in the art may be used by substituting or adding an insecticidal compound or compounds of this invention into the compositions known or apparent to the art.

The insecticidal compounds of this invention may be formulated and applied with other compatible active agents including nematicides, insecticides, acaricides, fungicides, plant regulators, herbicides, fertilizers, and the like.

In applying these compounds, whether alone or with other agricultural chemicals, an effective insecticidal, acaricidal or nematicidal amount of the active ingredient must be applied. While the application rate will vary widely depending on the choice of compound, formulation, mode of application, plant species being protected, planting density, and other like factors, a suitable use rate for agricultural crops may be in the range of 0.1 to 5 kg/ha, preferably 0.25 to about 2 kg/ha.

The following tests illustrate the biological activity of the compounds of this invention.

Foliar Application Test

The test compound was dissolved in 5–10 ml of acetone containing 0.25% octylphenoxypolyethoxyethanol. This solution was dispersed in a solution of 90% water, 9.75% acetone, and 0.25% octylphenoxypolyethoxyethanol to give a solution having either 1250 ppm or 1200 ppm (w/w) active ingredient. This solution was used as such or aliquots of it were diluted with an appropriate amount of water to provide solutions containing a desired amount of active ingredient.

Test organisms and techniques were as follows: The activity against Mexican bean beetle (*Epilachna varivestis* Muls.) and southern armyworm (*Spodoptera eridania* [Cram.]), was evaluated by spraying the leaves of pinto bean plants with the test solution and infesting with 3rd instar larvae after the foliage had dried. The activity against the pea aphid (*Acrythosiphon pisum* [Harris]) was evaluated on broad bean plants the leaves of which were sprayed before infestation with adult aphids. The activity against twospotted spider mites (*Tetranychus urticae* [Koch]) was evaluated on pinto bean plants the leaves of which were sprayed with test solution after infestation with adult mites. To prevent escape of the insects from the test site, the complete test plant or the incised leaves were placed in capped paper cups. The tests were transferred to a holding room at 80° C. and 50% relative humidity for an exposure period of 48 hours. At the end of this time the dead and living insects were counted and the percent kill was calculated.

Results of these tests are as follows: Compound 1 provided complete control of Mexican bean beetle and southern armyworm at 1200 ppm. Compound 2 provided complete control of southern armyworm at 1200 ppm. Compound 3 provided complete control of pea aphid at 1250 ppm, of southern armyworm at 1200 ppm, 95% control of Mexican bean beetle at 1200 ppm and 84 percent control of spider mite at 16 ppm. Compound 4 provided complete control of Mexican bean beetle, pea aphid and southern armyworm at 1000 ppm.

Comparative Foliar Test

In the manner of the foliar application test described above, compounds of the invention were tested for initial and 3-day residual activity against Mexican bean beetle and southern armyworm. Included in these tests were the corresponding S-propyl or S-s-butyl analogs of the compounds of the invention. The initial activity was measured as described in the Foliar Application Test above. The residual data were collected in the same manner except that the treated plants were infested 3 days after application of the test compound. The reference compounds are identified as follows, based on formula I above:

| Compound | $R^1$ | $R_a$ | $R_b$ | $R_c$ | $R_d$ |
|---|---|---|---|---|---|
| A | propyl | Cl | Cl | H | H |
| B | s-butyl | Cl | Cl | H | H |
| C | propyl | Cl | Br | H | H |
| D | s-butyl | Cl | Br | H | H |
| E | propyl | Cl | Cl | Cl | H |
| F | s-butyl | Cl | Cl | H | Cl |
| G | s-butyl | Cl | Cl | H | Cl |

The results, reported in Table I clearly show the superiority of the compounds of the invention over the reference compounds with respect to 3 day residual activity.

TABLE 1

| | Percent Mortality | | | |
|---|---|---|---|---|
| | Southern Armyworm | | Mexican Bean Beetle | |
| Compound | Initial Activity 500 ppm | Residual[c] Activity 1000 ppm | Initial Activity 1000 ppm | Residual[c] Activity 1000 ppm |
| 1 | 100 | 25 | 100 | 95 |
| A | 100 | 0 | 85 | 0 |
| B | 95 | 10 | 95 | 60 |
| 2 | 100 | 100 | 100 | 90 |
| C | 100 | 20 | 85 | 5 |
| D | 100 | 0 | 100 | 95 |
| 3 | 100 | 75 | 85[a] | 75[a] |
| E | 95 | 0 | 85[a] | 0[a] |
| 4 | 100 | 70 | 100[a] | 70[a] |
| F | 100 | 0 | 90[a] | 0[a] |
| G | 80 | 0 | 95[a] | 0[a] |

[a] = 500 ppm
[c] = at 3 days

Foliar Tests for Initial and Residual LC$_{50}$

Additional foliar tests were performed as in the comparative foliar tests above except that several concentrations of the test compound were employed to determine the initial and residual LC$_{50}$ (the concentration at which 50 percent of the test organisms are killed) against Mexican bean beetle, southern armyworm, and twospotted spider mite over a period of several days. The reference compounds were also included for comparative purposes. In evaluating LC$_{50}$ data, compounds having a lower LC$_{50}$ value are more active than those having a higher LC$_{50}$ value. The test results for Mexican bean beetle, southern armyworm and twospotted spider mite are set forth in Tables II, III, and IV, respectively. In those tables numbers enclosed in parentheses indicate percent mortality at the indicated concentration.

TABLE II

| Compound | LC$_{50}$ Against Mexican Bean Beetle (ppm at — days after application) | | | | |
|---|---|---|---|---|---|
| | 0 | 1 | 3 | 5 | 7 |
| 1 | 125 | — | 96.6 | — | >600(30%) |
| A | 1092 | — | >1800(5%) | — | — |
| 2 | 88 | — | 175 | — | 182 |
| C | 135 | — | 1469 | — | 2258 |

TABLE II-continued

| Compound | LC$_{50}$ Against Mexican Bean Beetle (ppm at — days after application) | | | | |
|---|---|---|---|---|---|
| | 0 | 1 | 3 | 5 | 7 |
| 2 | 100 | 125 | 140 | 170 | 480 |
| C | >150 (10%) | 673 | >1600(35%) | >2000(10%) | — |

TABLE III

| Compound | LC$_{50}$ Against Southern Armyworm (ppm at — days after application) | | | | |
|---|---|---|---|---|---|
| | 0 | 1 | 3 | 5 | 7 |
| 1 | 102 | — | 676 | — | >1200(5%) |
| A | 154 | — | >1200(15%) | — | — |
| 2 | 100 | 101 | 349 | 549 | >800(25%) |
| C | 37 | 207 | 1090 | >2000(45%) | >2000(0%) |

TABLE IV

| Compound | LC$_{50}$ Against Twospotted Spider Mite (ppm at — days after application) | | | | |
|---|---|---|---|---|---|
| | 0 | 1 | 3 | 5 | 7 |
| 2 | 3.9 | 37 | 106 | 169 | 367 |
| C | 1.5 | >100(19%) | >100(2%) | >500(15%) | >1000(0%) |

Compounds 1 and 2 of the invention were both clearly superior to reference compounds A and C against all three species.

Mite Ovicide Test

Leaves of growing pinto bean seedlings were infested with mites; two to four hours later, when female mites had deposited eggs, adult mites were killed on plant leaves by treatment with an aqueous solution of tetraethyl pyrophosphate (TEPP) (936 ppm active ingredient). After an additional two to four hours leaves were sprayed with aqueous-acetone solution of the toxicant. Seven days after plant infestation, a count of unhatched eggs and dead and living larvae was taken.

Compounds 1 and 2 of the invention provided 100% control at 100 ppm. Compound C provided 28% control at that level, and chlordimeform, a commercial ovicide, provided only 10 percent control at 100 ppm.

I claim:

1. An O-halophenyl O-ethyl S-alkyl phosphorothioate compound of the formula

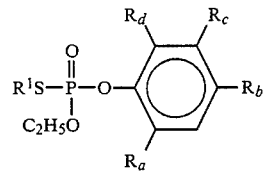

in which
$R^1$ is tertiary butyl,
$R_a$ and $R_b$ are each bromine or chlorine,
$R_c$ is hydrogen, chlorine or bromine,
$R_d$ is hydrogen, chlorine or bromine.

2. The compound of claim 1 in which said O-halophenyl group is 2,4-dichlorophenyl, 2,4,5-trichlorophenyl, 2,4,6-trichlorophenyl or 4-bromo-2-chlorophenyl.

3. The compound of claim 2 in which said O-halophenyl group is 2,4-dichlorophenyl.

4. The compound of claim 2 in which said O-halophenyl group is 4-bromo-2-chlorophenyl.

5. A method for control of foliar feeding insects which comprises applying to the above ground portions of a plant an insecticidal amount of the compound of claim 1, 2, 3, or 4.

6. A method for control of acarids which comprises applying to the above ground portions of a plant an acaricidal amount of the compound of claim 1, 2, 3, or 4.

7. An insecticidal and acaricidal composition comprising an insecticidal and acaricidal amount of the compound of claim 1, 2, 3, or 4, in admixture with at least one agriculturally acceptable carrier, diluent, or vehicle.

* * * * *